United States Patent
Nachtman et al.

[11] Patent Number: 6,024,971
[45] Date of Patent: *Feb. 15, 2000

[54] WATER FOG FOR REPELLING BIRDS

[76] Inventors: Thomas J. Nachtman, 8119 Comanche Trail, Temperance, Mich. 48182; John H. Hull, 3554 Edgevale Rd., Toledo, Ohio 43606; Larry Clark, 3701 Kentford Rd., Ft. Collins, Colo. 80525

[*] Notice: This patent issued on a continued prosecution application filed under 37 CFR 1.53(d), and is subject to the twenty year patent term provisions of 35 U.S.C. 154(a)(2).

[21] Appl. No.: 08/834,585

[22] Filed: Apr. 7, 1997

Related U.S. Application Data

[63] Continuation of application No. 08/510,926, Aug. 3, 1995, abandoned.

[51] Int. Cl.[7] ................................................. A01N 25/00
[52] U.S. Cl. .......................................... 424/405; 424/400
[58] Field of Search .................................... 424/400, 405

[56] References Cited

U.S. PATENT DOCUMENTS

| | | | |
|---|---|---|---|
| 2,967,128 | 1/1961 | Kare | 167/46 |
| 3,722,815 | 3/1973 | Moore | 239/2 R |
| 4,663,315 | 5/1987 | Hasegawa et al. | 514/86 |
| 4,790,990 | 12/1988 | Mason et al. | 424/438 |
| 5,061,478 | 10/1991 | Yarkony et al. | 424/45 |
| 5,187,196 | 2/1993 | Cummings et al. | 514/535 |
| 5,290,557 | 3/1994 | Mason et al. | 424/410 |
| 5,466,674 | 11/1995 | Preiser et al. | 514/23 |
| 5,549,902 | 8/1996 | Preiser et al. | 424/405 |

OTHER PUBLICATIONS

Monell, Published Patent Application, Aug. 8, 1991.
Nachtman, "New and Improved Bird Control Techniques at Landfills", 1993.
ReJeX–iT AP–50, Technical Bulletin, 1992.
ReJeX–iT TP–40 Bird Aversion Product, Jan. 1994.
Wildlife Control Procedures Manual, 1992.
New Encyclopaedia Britannica, vol. 11, p. 599, 1992.
Encyclopedia Americana, vol. 26, p. 353, 1990.

*Primary Examiner*—Jose' G. Dees
*Assistant Examiner*—Kathryne E. Shelborne
*Attorney, Agent, or Firm*—MacMillan, Sobanski & Todd, LLC

[57] ABSTRACT

In a method of repelling birds from an area, a fog is formed from a mixture comprising water and a chemical bird aversion agent. Preferably the mixture also includes a dispersant. The water fog can be formed by heating and/or pressurizing the so that it vaporizes. After it is formed, the water fog is directed into the atmosphere toward the birds to be repelled.

12 Claims, 1 Drawing Sheet

WATER FOG FOR REPELLING BIRDS

This application is a continuation of copending application Ser. No. 08/510,926 filed on Aug. 3, 1995, now abandoned.

BACKGROUND OF THE INVENTION

This invention relates to a method of delivering a repelling agent to an area occupied by birds so as to effectively drive the birds away from that area.

Large numbers of birds are attracted to working landfills, airports, marinas, fish ponds, feed lots, golf courses and other large areas, creating a nuisance and human health hazards. The method of delivering a repelling agent established herein decreases the attractiveness of the area being protected to the birds so that the birds are driven to alternative areas, thus reducing conflict between humans and birds.

Numerous techniques for repelling birds from such areas have been used. These techniques include the use of pyrotechnics, bird distress calls, noise makers, visual deterrents such as hawk kites or balloons, and combinations of these methods. Though widely used, these methods are generally ineffective in repelling birds from a given area for more than relatively short periods of time, as the birds become habituated to whichever method or methods are selected. Periodically lethal methods must be used to reinforce other traditional bird control techniques.

It is also known to use chemical bird aversion agents to repel birds from a particular material treated with such agents. For example, chemical bird aversion agents have been used as a feed additive to deter birds from consuming otherwise edible materials, and as a coating to deter birds such as chickens from pecking and injuring one another.

All the methods suggested previously for repelling birds using chemical bird aversion agents rely on the birds ingesting the chemical agents. The methods are ineffective if the birds do not happen to feed on or peck on the treated objects.

Further, ingestion of the chemical bird aversion agents by the birds is a relatively inefficient mode of delivery for at least two reasons. First, chemical bird aversion agents are chemoirritants that work by stimulating the birds' trigeminal system (their facial sensory nerve system). If it is ingested, most of the chemical agent never accesses the receptors of the birds responsible for translating the physiological repellent signal to a behavioral response. The majority of the chemical agent passes to the gut where it is irrelevant as a warning signal.

Second, good chemical bird aversion agents are typically nonpolar and thus have low water solubility. These chemical agents can easily pass through the lipid layers at the receptor sites of the trigeminal system, but they generally are poor at passing through aqueous environments such as the mucous membrane linings in the mouth of a bird.

Because ingestion is an inefficient mode of delivery, it suffers from the drawback that high concentrations of chemical bird aversion agent are required to produce the desired repellent effect.

In a different field, chemical fogging has been used to kill insects such as mosquitoes. A chemical fog consists of an organic solvent such as a volatile hydrocarbon, and a chemical agent such as an insecticide dissolved in the solvent. However, due to environmental regulatory restrictions the use of volatile, hydrocarbon-based solvents has recently come under strict control.

In view of the drawbacks associated with relying on birds to ingest the chemical bird aversion agents, it would be desirable to provide an effective method of repelling birds regardless of whether or not the birds attempted to feed on or peck on treated objects. It would also be desirable to provide a method which does not require high concentrations of chemical bird aversion agent to be effective. It would also be desirable to provide a method to which birds are not readily habituated, so that such method was effective in repelling birds from an area for relatively long periods of time. It would also be desirable to provide a method which does not require the use of organic solvents.

SUMMARY OF THE INVENTION

This invention provides a method of repelling birds from an area. A fog is formed from a mixture comprising water and a chemical bird aversion agent. Preferably the mixture also includes a dispersant. The water fog can be formed by heating and/or pressurizing the mixture so that it vaporizes. After it is formed, the water fog is directed into the atmosphere toward the birds to be repelled. The water fog efficiently delivers minute quantities of high concentration of chemical bird aversion agent to the receptor sites of the birds' trigeminal system, irrespective of the birds' behavior. Because the chemical bird aversion agent is of high concentration, it will more easily pass through the polar biological protective barrier in the nose, mouth and eyes of the birds, thus effectively delivering the chemical agent to the receptor sites. The water fog eventually deposits on the surface of the surrounding area and is effective in repelling birds from that area over a long period of time. Moreover, the birds do not become readily habituated to the chemical bird aversion agent. The water fog is environmentally friendly because it uses water as a carrier medium instead of the volatile hydrocarbon solvents used in chemical fogs.

Various objects and advantages of this invention will become apparent to those skilled in the art from the following detailed description of the preferred embodiment.

DETAILED DESCRIPTION OF THE PREFERRED EMBODIMENT

Figure 1:
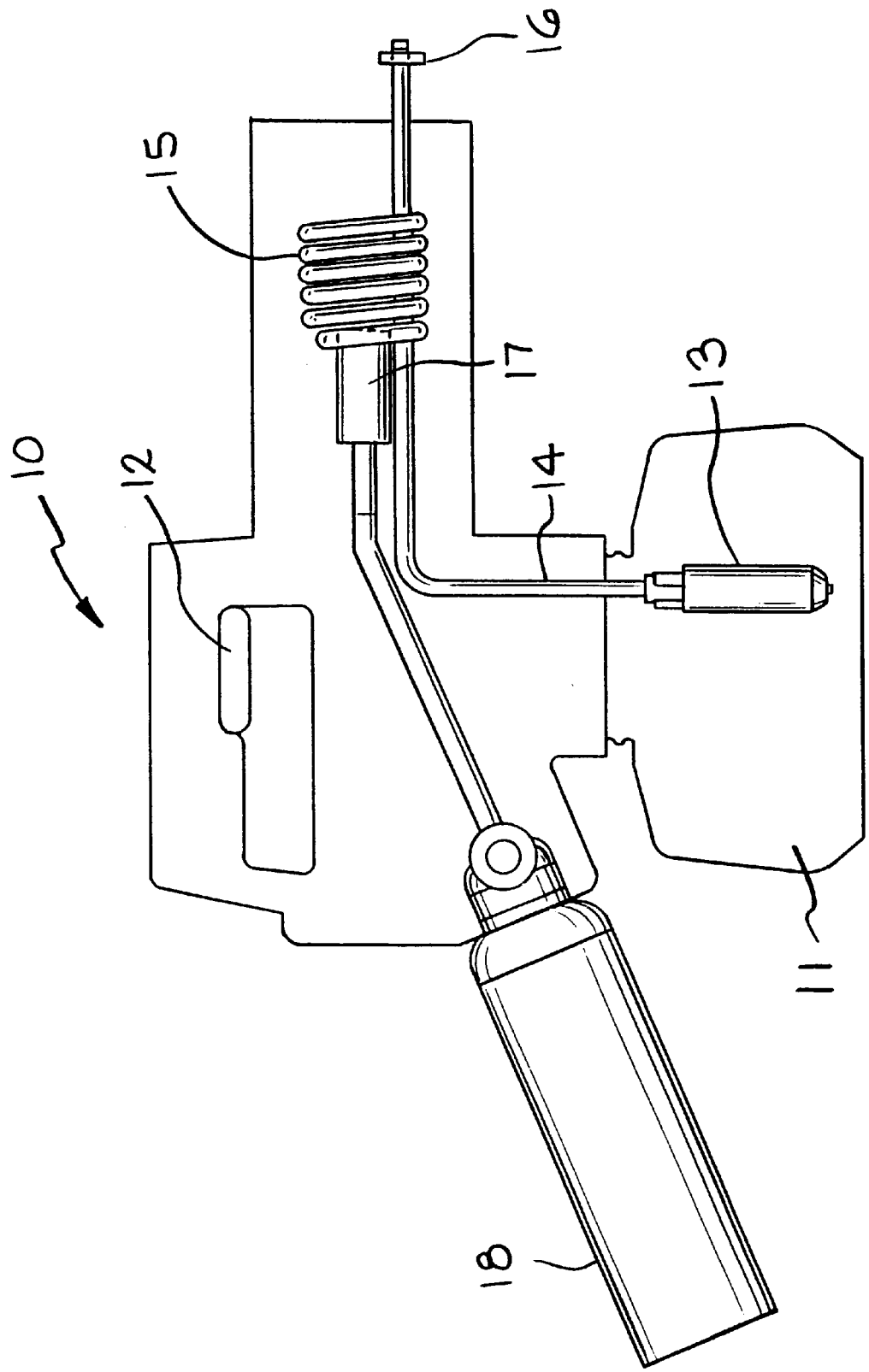
FIG. 1 is a schematic view of a fogging device useful in the practice of this invention.

This invention relates to a method of repelling birds from an area. In a preferred embodiment of this invention, birds may be repelled or driven away from an area by delivering a chemical bird aversion agent to the birds in an amount effective to repel at least about 50%, and preferably at least about 90% of the birds in that area. The birds will be at least temporarily repelled from the area upon the first application, and will generally be permanently repelled from the area upon an additional two or three applications on consecutive days. Their behavior can be modified to avoid the fogger itself.

The present method of repelling birds from an area comprises the steps of forming a fog from a mixture comprising water and a chemical bird aversion agent, and directing the fog toward the birds to be repelled. The birds are contacted with the fog to repel the birds from the area. A water fog can be created in any suitable manner, but preferably it is formed by heating and/or pressurizing the mixture to vaporize it and produce a fog of droplets suspended in the air.

When heating is used to create the water fog, it is preferably formed by the steps of: (a) forming a mixture of water and chemical bird aversion agent; (b) introducing the mixture into a chamber; (c) heating the mixture to a temperature sufficient to vaporize the mixture; and (d) releasing the mixture from the chamber to form a fog of the mixture.

A mosquito fogger type device can be used to create the fog, such as the Model 1443 Portable Propane Insect Fogger available from Burgess Products of Chadwicks, New York. The fogging device is modified to include a heat source capable of vaporizing the mixture, at a temperature around 212° F. (100° C.) depending on the types and amounts of chemical bird aversion agent and dispersant in the water.

Referring now to FIG. 1, there is illustrated a schematic view of a fogging device such as the above-mentioned mosquito fogger. In such a fogging device, indicated generally at 10 in the figure, the mixture of water and chemical bird aversion agent is stored in a reservoir 11. In response to activation of a trigger 12, a pump 13 forces the solution from the reservoir 11 through a passageway 14. The passageway 14 communicates with a heat-conducting coiled chamber 15, which in turn communicates with a small orificed outlet nozzle 16. A burner assembly 17, connected to a fuel source 18, is positioned adjacent the coiled chamber 15. When lit, the burner assembly 17 heats the chamber 15.

When the mixture is injected into heated chamber 15, the mixture is vaporized with a corresponding increase in volume and pressure. The expansion of the mixture from a liquid to a gas in the chamber 15 forces the mixture out through the small orifice of the nozzle 16, and into the atmosphere. Thus, a fog consisting of droplets of water and chemical bird aversion agent is created in the atmosphere beyond the nozzle 16 of the device 10.

When pressure is used to create the water fog, it is preferably formed by the steps of: (a) forming a mixture of water and chemical bird aversion agent; (b) introducing the mixture into a chamber; (c) pressurizing the mixture to a pressure sufficient to vaporize the mixture; and (d) releasing the mixture from the chamber to form a fog of the mixture.

A pressure washer, such as those used in landfills for cleaning, can be employed to create a water fog. The pressure washer can be used with or without heat.

Other insect fogging devices that can be used to create a water fog include those manufactured by Curtis Dyna-Fog Ltd., Westfield, Ind.

As mentioned hereinabove, the water fog of the invention is formed from a mixture comprising water and a chemical bird aversion agent. The mixture preferably comprises from about 0.1% to about 99% by weight water and from about 0.01% to about 99% by weight chemical bird aversion agent, more preferably from about 50% to about 99% water and from about 0.01% to about 50% chemical bird aversion agent, and most preferably from about 80% to about 99% water and from about 0.01% to about 20% chemical bird aversion agent. Because of the efficient method of this invention of delivering a chemical bird aversion agent, only a low concentration of chemical bird aversion agent is needed for repelling birds.

Any effective chemical bird aversion agent is suitable for use in this invention. Examples of such bird aversion agents include the anthranilates, esters of phenyl acetic acid, dimethyl benzyl carbinyl acetate, ortho amino benzoic acid derivatives, cinnamic acid derivatives, including the following: alpha- aminoacetophenone, ortho-arminoacetophenone, meta-aminoacetophenone, para-aminoacetophenone, ortho-hydroxyacetophenone, ortho-methoxyacetophenone, meta-methoxyacetophenone, para-methoxyacetophenone, 4-aminobenzoic acid, and 4-ketobenztriazine. Preferred chemical bird aversion agents for use with this invention include methyl anthranilate (MA) and di-methyl anthranilate (DMA), with MA being most preferred. Mixtures of the chemical bird aversion agents can also be used.

The mixture for forming the water fog preferably also includes a dispersant. The dispersant is believed to enhance the effect of the chemical bird aversion agent. The dispersant also aids in mixing the chemical bird aversion agent with the water. Suitable dispersants for use in this invention include, but are not limited to, yucca, lecithin, soybean oil, surfactants, and mixtures thereof. Preferred dispersants are yucca, lecithin, and soybean oil, with yucca being most preferred. Different types of lecithins can be used as the dispersant. The dispersant is preferably a food grade material.

Preferably the mixture comprises from about 0.1% to about 90% by weight dispersant, more preferably from about 0.1% to about 50% dispersant, and most preferably from about 0.1% to about 20% dispersant.

A specific preferred composition for forming the water fog is a mixture of 200 gallons of water, 2 ½ gallons of methyl anthranilate, and 1 gallon of yucca.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method of repelling birds from an area comprising:
producing a fog of droplets suspended in the air over the area, the fog comprising a mixture of from about 50% to about 99% by weight water, from about 0.01% to about 50% by weight chemical bird aversion agent, and from about 0.1% to about 50% by weight yucca, and
contacting the birds with the fog of droplets suspended in the air to repel the birds from the area.

2. The method defined in claim 1 wherein the fog comprises a mixture of from about 80% to about 99% by weight water, from about 0.01% to about 20% by weight chemical bird aversion agent, and from about 0.1% to about 20% by weight yucca.

3. The method defined in claim 1 wherein the area is a landfill.

4. The method defined in claim 1 wherein the chemical bird aversion agent is an anthranilate.

5. A method of repelling birds from an area comprising:
producing a fog of droplets suspended in the air over the area, the fog comprising a mixture of from about 50% to about 99% by weight water and from about 0.01% to about 50% by weight chemical bird aversion agent, the fog containing no organic solvent, and
contacting the birds with the fog of droplets suspended in the air to repel the birds from the area.

6. The method defined in claim 5 wherein the fog comprises a mixture of from about 80% to about 99% by weight water and from about 0.01% to about 20% by weight chemical bird aversion agent.

7. The method defined in claim 5 wherein the area is a landfill.

8. The method defined in claim 5 wherein the fog additionally comprises from about 0.1% to about 20% by weight dispersant.

9. A method of repelling birds from an area comprising:
forcefully ejecting a fog of droplets into the air over the area, the fog becoming suspended in the air, and the fog comprising a mixture of from about 50% to about 99% by weight water and from about 0.01% to about 50% by weight chemical bird aversion agent, and contacting the birds with the fog of droplets suspended in the air to repel the birds from the area.

10. The method defined in claim 9 wherein the fog is produced by introducing the mixture into a heated chamber to vaporize the mixture, and the vaporized mixture is forcefully ejected from the chamber into the air.

11. The method defined in claim 9 wherein the fog is produced by introducing the mixture into a chamber, and pressurizing the chamber to vaporize the mixture, and the vaporized mixture is forcefully ejected from the chamber into the air.

12. The method defined in claim 9 wherein the fog is produced from at least 200 gallons of the mixture.

* * * * *